Figure 1:
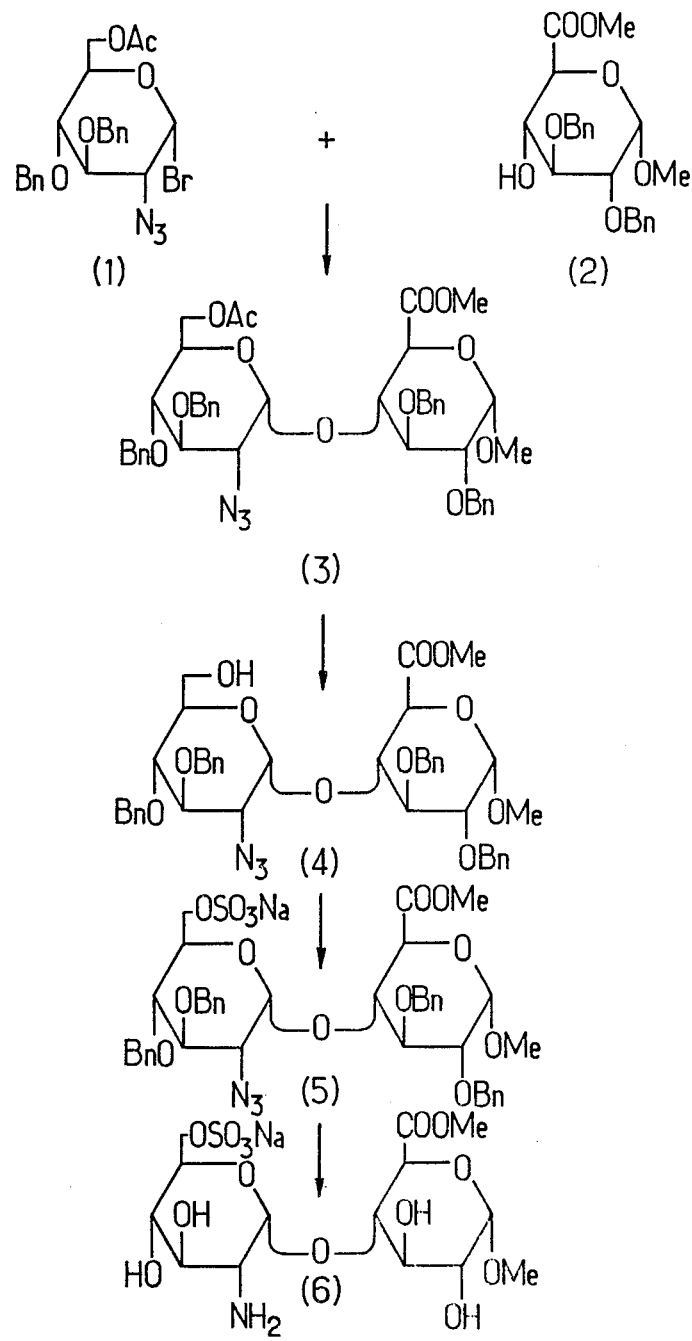

United States Patent [19]
Petitou et al.

[11] Patent Number: 4,774,231
[45] Date of Patent: Sep. 27, 1988

[54] DISACCHARIDES FORMED BY PATTERNS HAVING A GLUCOSAMINE AND URONIC ACID STRUCTURE, PREPARATION THEREOF AND BIOLOGICAL APPLICATIONS

[75] Inventors: Maurice Petitou, Paris; Pierre Sinay, Orleans; Jean Choay, Paris; Jean-Claude Lormeau, Maromme, all of France

[73] Assignee: Choay S.A., Paris, France

[21] Appl. No.: 888,527

[22] Filed: Jul. 21, 1986

Related U.S. Application Data

[63] Continuation of Ser. No. 451,615, Dec. 20, 1982, Pat. No. 4,607,025.

[30] Foreign Application Priority Data

Apr. 28, 1981 [FR] France .................. 81 08472

[51] Int. Cl.[4] ............................. A61K 31/70
[52] U.S. Cl. ........................ 514/53; 514/56; 514/62; 536/1.1; 536/4.1; 536/18.5; 536/18.6; 536/17.5; 536/118; 536/123; 536/124; 536/55.2; 536/55.3; 536/16.6
[58] Field of Search ............... 514/53, 56, 62; 536/4.1, 16.6, 1.1, 18.5, 2, 18.6, 55.2, 55.3, 17.5, 118, 123, 124; 549/415, 417

[56] References Cited

U.S. PATENT DOCUMENTS

| | | | |
|---|---|---|---|
| 2,374,236 | 4/1945 | Salzberg et al. | 536/18.6 |
| 4,098,995 | 7/1978 | Nair et al. | 536/118 |
| 4,303,651 | 12/1981 | Lindahl et al. | 536/21 |
| 4,362,720 | 12/1982 | Lemieux et al. | 536/123 |
| 4,401,662 | 8/1983 | Lormeau et al. | 536/17.5 |
| 4,401,758 | 8/1983 | Lormeau et al. | 536/55.3 |
| 4,413,120 | 11/1983 | Whistler | 536/17.5 |
| 4,435,387 | 3/1984 | Schaub et al. | 536/4.1 |
| 4,607,025 | 8/1986 | Petitou et al. | 536/123 |

FOREIGN PATENT DOCUMENTS 0014184 8/1980 European Pat. Off. .
0027089 4/1981 European Pat. Off. .
0048231 3/1982 European Pat. Off. .

OTHER PUBLICATIONS

Tetrahedron Letters No. 5, Klemer and Kraska, pp. 431-433, 1972.
Carbohydrate Research, vol. 78, No. 2, Klein, Jan. 15, 1980, pp. 249-256.
Tetrahedron Letters No. 30, Kiss and Wyss, pp. 3055-3058, 1972.
Bulletin de la Societe de Chimie Bilogique, Tome XLII, 1960, Nos. 9-10, Barker et al., Jan. 25, 1961.
Helvetica Chimica Acta, H.C.A., vol. 58, Fascs 6, Wyss et al., pp. 1847-1864 (1975).
IUPAC Pure & Applied Chemistry, vol. 50, Sinay, pp. 1437-1452, 1978, J. Chem. Soc., 1962, Turvey and Williams, pp. 2119-2122.
Organic Chemistry, 2nd Ed., Louis F. Fieser & Mary Fieser, pp. 229-233 (1950), D. C. Heath and Company, New York, N.Y.
Paulsen, Angew. Chem. Int. Ed. Engl., vol. 21, No. 3, Mar., 1982, pp. 155-224.

*Primary Examiner*—Ronald W. Griffin
*Attorney, Agent, or Firm*—Davis Hoxie Faithfull & Hapgood

[57] ABSTRACT

1,4αdisaccharides of formula:

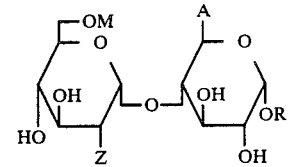

with
Z representing a nitrogenous functional group,
M hydrogen or a sulphate or acetyl group,
R an alkyl radical of 1 to 4 carbon atoms and
A functional group such as an acid group, or a derivative.

26 Claims, 4 Drawing Sheets

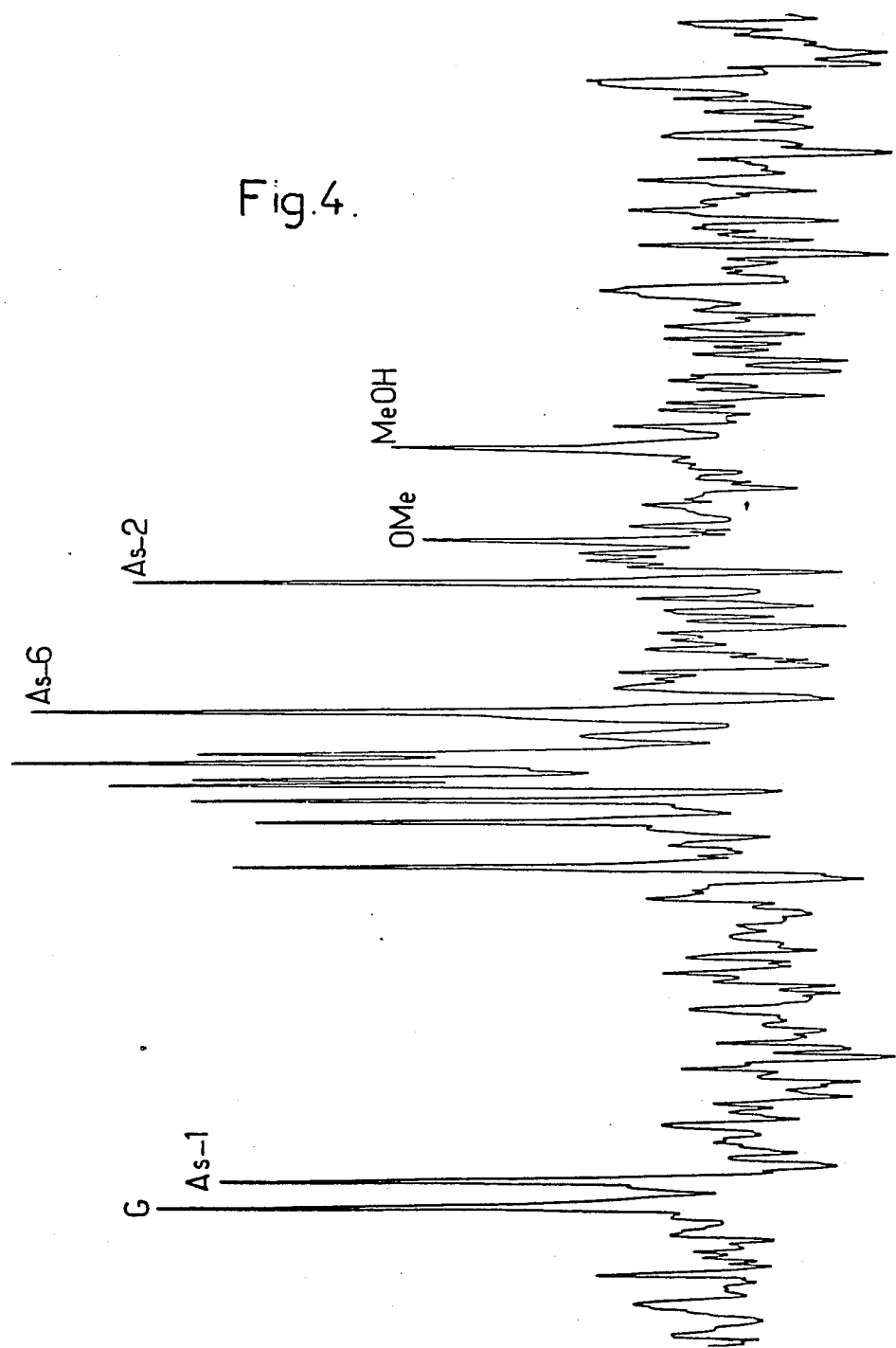

DISACCHARIDES FORMED BY PATTERNS HAVING A GLUCOSAMINE AND URONIC ACID STRUCTURE, PREPARATION THEREOF AND BIOLOGICAL APPLICATIONS

This is a continuation of application Ser. No. 451,615, filed Dec. 20, 1982, now U.S. Pat. No. 4,607,025.

The invention relates to novel disaccharides possessing, particularly, biological properties, formed from units with a glucosamine and a uronic acid structure, respectively.

It is directed, more especially, to 1,4 α disaccharides formed from units with a D-glucosamine and glucuronic acid structure.

It is directed also at their preparation, as well as their biological and biochemical applications, particularly as an active principle of medicaments.

These novel disaccharides correspond to the formula (I):

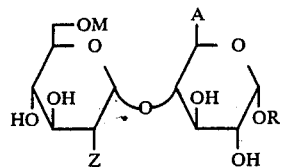

in which

Z represents a nitrogenous functional group, such as an azide group, or a group of the structure —NHB in which B represents a hydrogen atom or a functional group, such as an acetyl group or a sulphate group, possibly in the form of a salt with a organic or inorganic cation, and, in the latter case, in particular, an alkali cation, M represents a hydrogen atom or $-SO_3M_1$ group in which $M_1$ represents an organic or inorganic cation, and in the latter case, in particular an alkali metal, or represents an acetyl group;

R represents an alkyl radical of 1 to 4 carbon atoms, in particular, a methyl radical, or again aryl, and A represents a functional group such as an acid group, or a derivative of such a group, in particular, a group of the structure $-COOR_1$ in which $R_1$ represents a hydrogen atom, an alkyl radical comprising 1 to 4 carbon atoms, and in particular a methyl radical, or a metal, in particular, an alkali metal.

These disaccharides advantageously possess the structure of constituent units of heparin chains. They comprise, in fact, on the glucosamine unit a nitrogenous group at the 2 position and a primary alcohol group advantageously sulphated at the 6 position, and on the glucuronic acid unit an acid functional group or a derivative of an acid at the 6 position.

Preferred disaccharides have the formula (II):

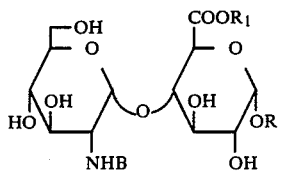

Other especially preferred disaccharides correspond to the formula (III):

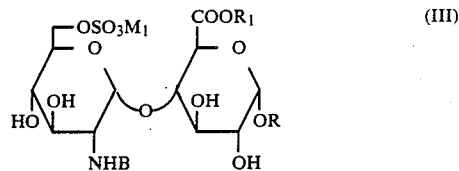

In these formulae B, R, $R_1$ and $M_1$ have the meanings given above, $M_1$ representing advantageously an alkali metal, in particular, sodium.

In preferred families of these disaccharides II and III, the substituent B represents an acetyl group. It relates therefore to families comprising an N-acetyl D-glucosamine unit. Other families of disaccharides of the invention comprise as glucosamine units, D-glucosamine N-sulphate. In these families, B represents an $-SO_3M_2$ group in which $M_2$, identical or different from $M_1$, represents a metal, in particular an alkali metal, more especially sodium.

Products of these families comprise substituents $R_1$ and R which are identical and represent an alkyl group, in particular a methyl or aryl group.

In other preferred products, these substituents are different and represent respectively an alkali metal, in particular, sodium ($R_1$) and alkyl radical, in particular methyl (R).

A product of this type more especially preferred corresponds to the formula (IV):

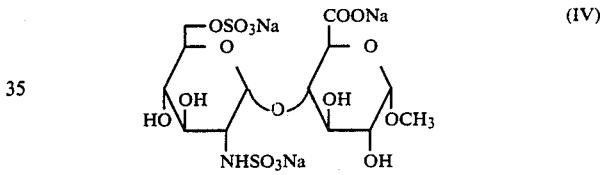

Pharmacological study of the disaccharides of the invention has shown that they possess, in particular, biological properties enabling them to control, specifically, certain stages of blood coagulation.

These products are shown in particular to be endowed with a selective inhibiting activity for the activated X factor or Xa factor of the blood, and this, more particularly as regards the disaccharides of formula (III), more especially those comprising D-glucosamine N-sulphate units.

They constitute, in this respect, reference reagents enabling comparative measurements aimed at evaluating the relative inhibiting activity of the Xa factor of the substances under study. The disaccharide of formula (IV) presents, for example, an anti-Xa activity, measured by the Yin-Wessler test, of the order of 1,000 to 2,000 u/g.

The Yin and Wessler test, which enables measurement of an activity more especially representative of the aptitude of products to potentiate the inhibition of the Xa factor of the blood by antithrombin III, or AT III, is described by these authors in J. Lab. Clin. Med. 1976, 81, pp 298 to 300.

These disaccharides may advantageously be used as active principle of a medicament for controlling the in vivo blood coagulation, in man or in an animal subject to risk of hypercoagulability, such as those induced by surgical operations, atheromatous processes, disturbances of the mechanism of coagulation by bacterial or enzymatic activators, etc., as a consequence of the liberation in the organism of thromboplastins, for example tissular thromboplastin.

The advantage of these disaccharides is further enhanced owing to their innocuousness.

The invention relates hence also to pharmaceutical compositions in which these compounds are asociated in an effective amount with a pharmaceutical vehicle.

It relates particularly to compositions in which the pharmaceutical vehicle is suitable for oral administration. Administrative forms of the invention suitable for oral administration may advantageously be gastro-resistant gelules, tablets or lozenges, pills, or again be present in the form of liposomes.

Other pharmaceutical compositions comprises these disaccharides in association with suitable excipients for administration rectally. Corresponding administrative forms are constituted by suppositories.

Other administrative forms of the invention are constituted by aerosols or ointments.

The invention relates also to injectable, sterile or sterilisable pharmaceutical compositions.

In order to illustrate the invention, there is indicated, below, an example of posology usable in man: this posology comprises, for example, the administration to the patient of 50 mg to 2 g of disaccharide, twice or thrice daily. These doses may naturally be adjusted for each patient according to the results and blood analyses carried out previously, the nature of the disorders from which he suffers and, generally, his state of health.

The invention relates also to the use of disaccharides of the invention, in the constitution of biological reagents, useful in laboratories, particularly as elements of comparison for the study of other substances of which it is desired to test the anti-coagulant activity, particularly at the level of inhibition of the Xa factor.

The invention relates also to a method of synthesizing the above-defined disaccharides.

According to this method, two monosaccharides are applied enabling (a) through their structure, (b) through the nature of their reactive groups, (c) through the nature of their blocking groups, the realisation of the synthesis strategy according to the invention.

The blocking groups are advantageously higher than 1 in number, they enable the introduction after unblocking, of functional groups as well as of specific substituent groups such as existing on the structure of the disaccharides of the invention, they are compatible with the reactive groups, they are capable of undergoing sequential unblocking, compatible one to the other and compatible with the substituents introduced at each step.

A condensation reaction is carried out between these two monosaccharides, in order to establish, the desired 1,4 α bond, under conditions compatible with the various substituents of the monosaccharides, then there follows by successive steps the introduction of functional groups and of the desired substituents for a given disaccharide by employing corresponding specific reactions.

The monosaccharides applied correspond respectively to formulae V and VI:

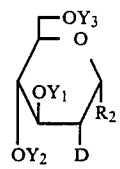
(V)

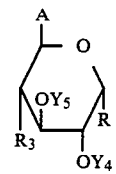
(VI)

In these formulae, $R_2$ and $R_3$ represent two reactive groups permitting the establishment, selectively, of a 1,4 α bond, these groups being selected from among those compatible with the other groups of the monosaccharides;

$Y_1$ to $Y_5$ represent blocking groups enabling, through their nature, the introduction successively of the desired functional groups without the remaining blocking groups being affected, and D represents a nitrogenous group which is a precursor of a nitrogenous functional group —NHB as defined above, preferably an azide group;

A and R have the above-mentioned meanings, A representing especially a —$COOR_1$ group with $R_1$ representing an alkyl radical or any other radical which can be eliminated to give rise to a —$COOM_1$ group as defined above.

According to a feature of great interest of the invention, the blocking group $Y_3$, which occupies a position intended to be sulphated, is constituted by a group enabling the realisation selectively of the sulphation operation without affecting the other groups. Preferably, $Y_3$ represents an acetyl group. The choice of a group of this type, more especially of an acetyl group, will also be effected, during the synthesis, for other positions intended to be sulphated, namely for B in —NHB.

In accordance with another feature, the blocking groups $Y_1$, $Y_2$, $Y_4$ and $Y_5$ which will be eliminated during the synthesis to liberate hydroxyl groups are constituted by benzyl groups.

In a preferred embodiment of the invention, the condensation reaction of the monosaccharides V and VI is based on the reaction of a halide with an alcohol function.

Advantageously a monosaccharide V is then applied in which $R_2$ represents a halide preferably a bromide, or again a chloride, with a monosaccharide VI in which $R_3$ represents a hydroxyl group.

This reaction is advantageously carried out in a solvent medium, in particular in an organic solvent of the dichloromethane type. Advantageously a catalyst is used, such as silver triflate and also a proton acceptor such as sym-collidine.

Then the disaccharide with the 1,4 α bond obtained of structure:

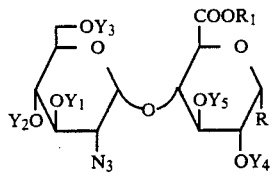

(VII)

is treated so as to introduce selectively and successively the desired functional groups.

In order to introduce a sulphate group in place of Y₃, the disaccharide VII is first subjected to a hydrolysis reaction under the action of a strong base such as soda, then the action of an alkylating agent in order to maintain a —COOR₁ group as substituent A.

The disaccharide obtained, which thus comprises a primary alcohol function —CH₂OH at the 6 position of the D-glucosamine unit, is subjected to the action of a sulphating agent under conditions enabling the —CH₂OH group to be replaced at the 6 position by a sulphate group without affecting the other blocking groups of the molecule as well as the azide group.

Advantageously there is used, for this purpose, a complex of trimethylamine and SO₃. The introduction of the desired cation M₁ may in particular be carried out by means of an ion exchange resin comprising this cation or again, after passage into acid form, by neutralisation with the base of the cation.

In the course of a following step, there then follows advantageously the release of the —OH groups blocked by Y₁, Y₂, Y₄ and Y₅ and the conversion of the group —N₃ into group —NH₂.

To this end, it is suitable to resort to a hydrogenation reaction, with hydrogen in the presence of a catalyst, by operating under conditions compatible with the maintenance of the sulphate group at the 6 position of the D-glucosamine unit.

According to a modified embodiment of the invention, a disaccharide is prepared including an N-acetyl D-glucosamide unit by treating the previously obtained disaccharide with an acetylating agent, in particular acetic anhydride.

Advantageously this takes place in weakly basic medium, at a pH of the order of 8 under conditions not affecting the other substituents of the disaccharide.

According to another embodiment of the invention, a disaccharide is prepared comprising a D-glucosamine N-sulphate unit by treating the disaccharide obtained after the hydrogenation step with a sulphating agent.

It appears appropriate to carry out this reaction at a basic pH between about 9 and 10, advantageously by means of a trimethylamine and SO₃ complex. To obtain this sulphate group, in the form of a salt, advantageously an ion exchange resin is used containing the cation that it is desired to introduce, or again, after passing into the acid form, it is neutralized with the base of the cation.

The treatment of the N-acetylated or N-sulphated produced mentioned above by a metal hydroxide enables the production, if desired, of the corresponding disaccharides including a carboxylate at the 6 position of the glucuronic unit. Advantageously soda is used to form the sodium carboxylate.

The intermediate disaccharides are novel products and as such enter also into the scope of the invention. It is the same for the monosaccharide (2) described in the Examples.

Figure 2:
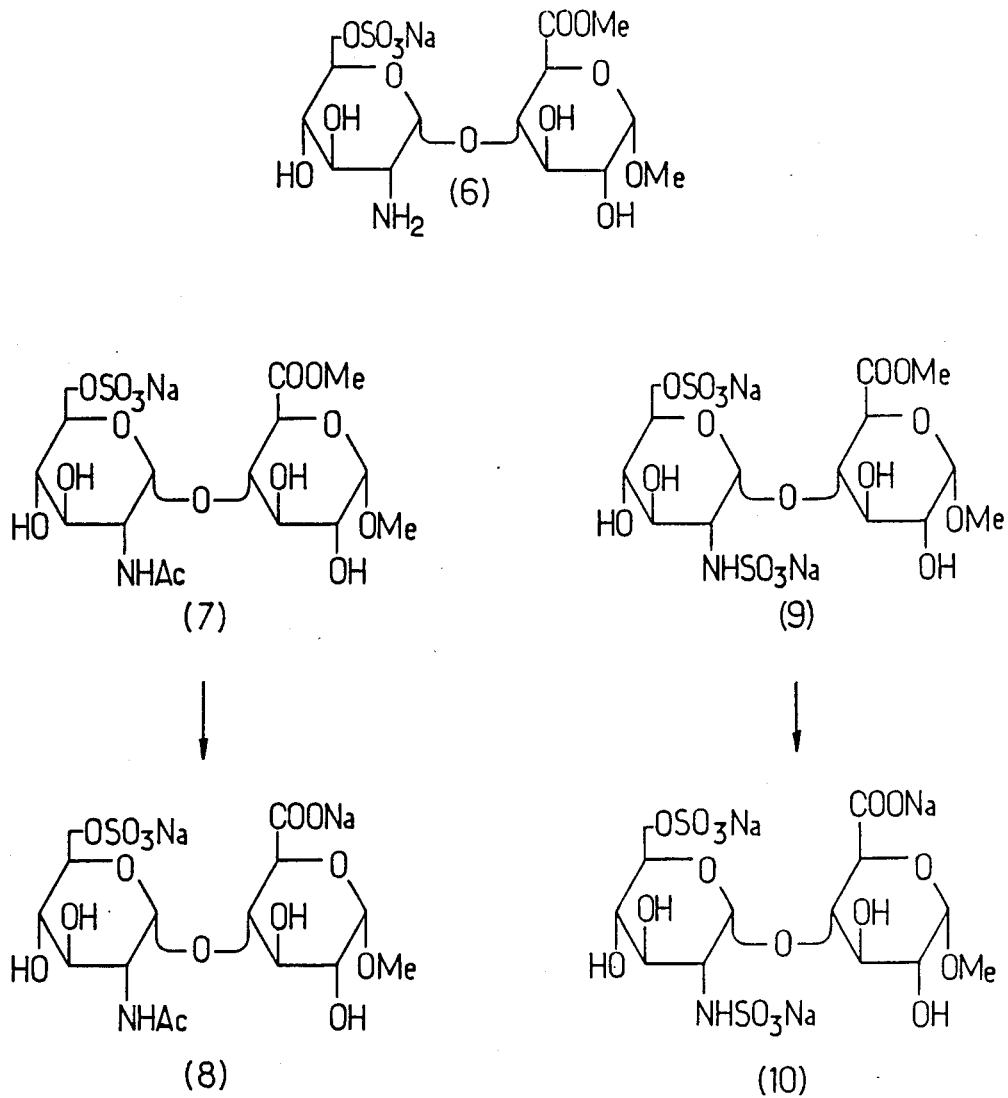
Figure 3:
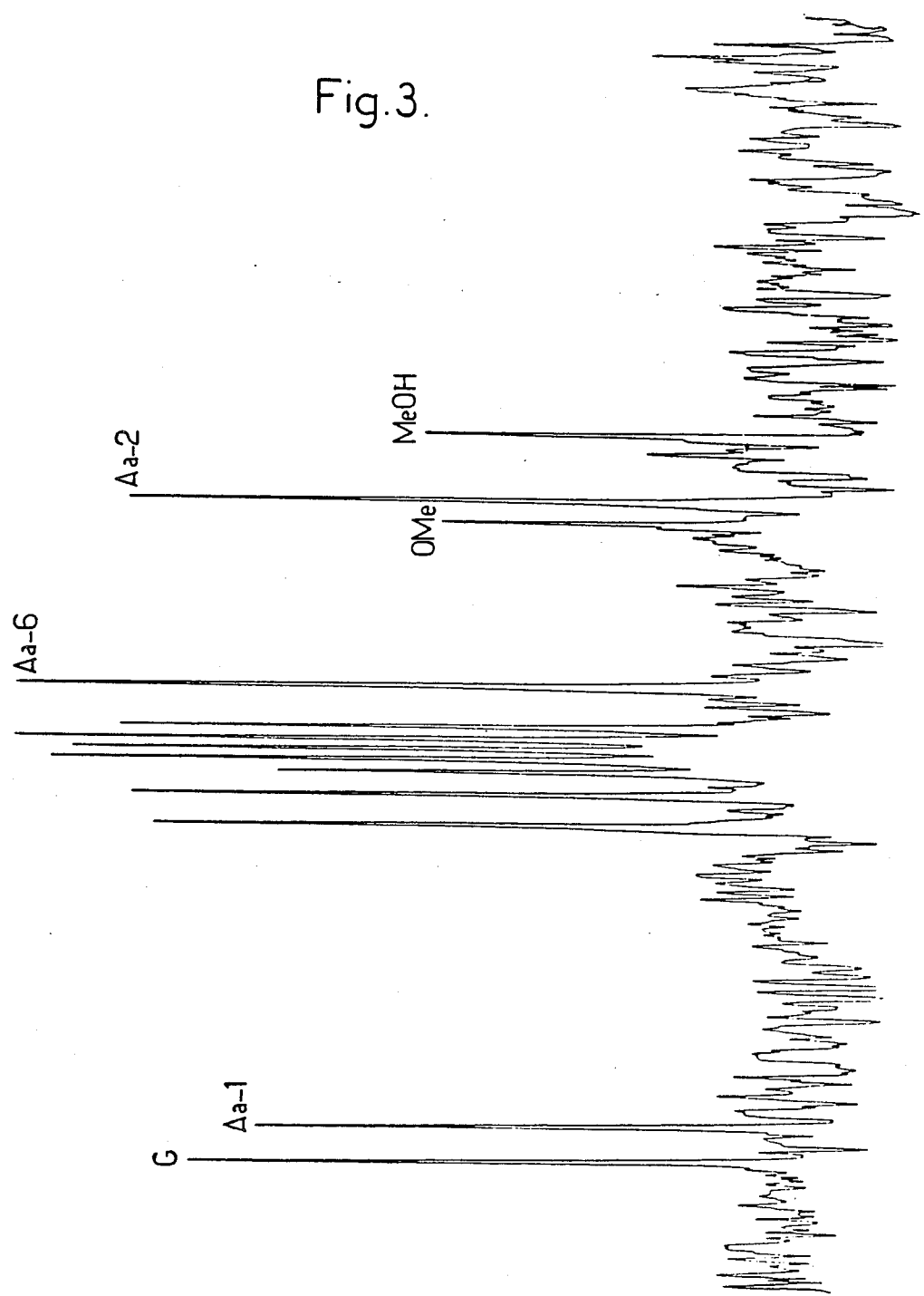

Other features and advantages of the invention will appear from the description of the Examples which follow and with reference to the Figures in which FIGS. 1 and 2 show the whole of the reaction diagram corresponding to the synthesis described in the Examples, and FIGS. 3 and 4 and NMR spectra of disaccharides of the invention.

The abbreviations used in the formulae have the following meanings:

Ac represents an acetyl group,
Bn a benzyl group and
Me a methyl group.

The compounds of FIGS. 1 and 2 are identified by numerical references between parenthesis, which are also used in the Examples to denote them.

EXAMPLE 1

Preparation of methyl (Methyl 2,3-di-O-benzyl-α-D-glucopyranoside)uronate

In 20 ml of methylene chloride, there is stirred in the dark for one night, a mixture of 0.75 g (2 mmole) of methyl 2,3-di-O-benzyl-α-D-glucopyranoside, 20 mg (0.08 mmole) of dimethyl-aminopyridine, 0.6 ml (4 mmole) of triethylamine and 0.84 g (3 mmole) of trityl chloride. Thin layer chromatography (methanol/chloroform: 0.2/20, v/v) shows that the reaction is complete The starting monosaccharide is prepared according to the method of Freudenberg K. and Plankenhorn E. described in Ber. Deut. Chem. Ges. 73 (1940) 621-631. Successively to this mixture 0.6 ml (4 mmole) of triethylamine, 0.35 ml (3 mmole) of benzoyl chloride, 50 mg (0.20 mmole) of dimethylaminopyridine are added and stirring is continued for two days.

To eliminate the trityl group, a solution of 0.5M of paratoluene sulphonic acid in methanol (20 ml) is added to the mixture. After one hour, the mixture is diluted with methylene chloride, then washed with water until neutrality. The product is purified by chromatography on a column (40 g) using an ether-hexane mixture (3/1, v/v).

A pure white foam is obtained (0.84 g; 87.7%) which is immediately oxidized by the method of Kovac P., Alföldi J., Kosik M. described in Chem. Zvesti 28 (1974) 820-832.

480 mg (1 mmole) of the product is dissolved in 8 ml of acetone and to the cooled solution there is added at 0° C., with stirring, a solution of chrome VI oxide in sulphuric acid 3.5M (1.15 ml of chromium solution contains 1.17 g in 5 ml).

The mixture is left to recover room temperature, and then after two hours, ice and water are added and the product extracted with chloroform. The chloroform phase is washed with water and the dried solvent is evaporated.

The foam obtained is dissolved in methanol (10 mg/ml) and soda (5 ml of a 3M solution) is added. After three hours, the aqueous phase is washed twice with ether then acidified with hydrochloric acid. The product is then extracted with ether. The organic phase is washed with water, dried and concentrated.

The solution so obtained is methylated with diazomethane in ether and purified on a column of silica gel (15 g) in an ether-hexane mixture (2/1; v/v).

Yield: 233 mg, 57.9%.

The compound is crystallised in a hexane-ether mixture and has the following characteristics:

M.P.: 82° C.; $(\alpha)_D^{20}$: +17.5 (c=1; chloroform);

Spectra $^1$H RMN (Me$_4$Si; internal reference) δ 2.9 (d, 1H, OH) 3.35 (s, 3H, OCH$_3$) 3.69 (s, 3H, COOCH$_3$) 7.27 (12H, 2 Ph).

Analysis: calculated for $C_{22}H_{26}O_7$: C, 65.65; H, 6.51; found: C, 65.53; H, 6.29.

EXAMPLE 2

Preparation of the disaccharide (3)

The synthesis of this disaccharide (3) is carried out from monosaccharides (1) and (2) by proceeding as follows. The reaction is carried out at 0° C. under nitrogen and protected from light.

To a solution of the compound (2) (40 mg) in dichloromethane (2 ml), are added successively the compound (1) (98 mg), sym-collidine (35 μl) and silver triflate (56.5 mg). After one hour and a half, the reaction mixture is diluted with dichloromethane (50 ml). The solution is filtered, washed with saturated sodium bicarbonate (twice 20 ml), then with water and finally dried.

The syrup obtained after concentration is chromatographed on silica gel (15 g) in the system ethyl acetate/hexane (1.3, v/v).

In this way the disaccharide (3) is obtained (60.2 mg; 74%).

The NMR spectrum confirms the required structure: signals observed (with respect to Me$_4$Si, internal standard), δ 1.95 (s, 3H, —OCOCH$_3$) 3.34 (s, 3H, OCH$_3$) 3.68 (s, 3H, CO—O—CH$_3$) 5.53 (d, 1H, 3, 5 Hz, H'-1) 7.20–7.40 (m, 20H, 4 Ph).

EXAMPLE 3

Preparation of the disaccharide (6)

In the first step (a), a saponification of the —OAC group is carried out at the 6 position of the D-glucosamine unit, then step (b) follows with the sulphation of the —OH group at the 6 position, and in the course of a hydrogenation step (c), blocking groups Bn are removed and simultaneously the —N$_3$ group is converted into an —NH$_2$ group.

a—preparation of disaccharide (4) by saponification—

The compound (3) is dissolved in methanol (10 ml), then 1N soda (2 ml) is added. After three hours, the solution was neutralized by passage over Dowex resin 50 W×4 H$^+$ (5 ml). After concentration, the residue was methylated by diazomethane, in order to reintroduce the methyl group removed at the same time as the acetate. In this way the compound (4) is obtained.

b—preparation of disaccharide (5) by sulphation—

The compound (4) was dissolved in anhydrous DMF (3 ml). Then the complex trimethylamine/SO$_3$ (20 mg) is added and it is left at 65° C. After one night, the mixture was evaporated to dryness, taken up again with chloroform, diluted with methanol, then passed over a DOWEX 50—Na$^+$ resin. The organic phase was washed with water, dried, then the chloroform was evaporated. The compound (5) (40 mg) was obtained.

c—preparation of the disaccharide (6) by hydrogenation—

The compound (5) is dissolved in methanol (10 ml) and water (1 ml). 40 mg at 5% Pd/C was added and it was subjected to the action of hydrogen for 48 hours. After filtration and evaporation, the compound (6) (29 mg) was obtained.

EXAMPLE 4

Preparation of disaccharides (7) and (8)

These derivatives were prepared by subjecting the disaccharide (6) to an acetylation reaction of the —NH$_2$ group of the unit with the glucosamine structure, followed by saponification of the —COOMe group of the unit with the uronic acid structure. The compound (6) (14 mg) was dissolved in methanol (3 ml). The pH was adjusted to 8 with 1N soda. Then acetic anhydride (100 μl) was added. After 30 minutes, it was evaporated to dryness. The residue was dissolved in water (1.5 ml) and 1N soda was added (0.5 ml). After one night at ambient temperature, the solution was neutralized with hydrochloric acid. The product was then desalted by passage over a Sephadex G-25 column (1.8×20 cm). The fractions containing the product were collected and chromatographed on an anion exchange resin (AG 1×2 200–400 mesh; bed of 1 ml). The products were eluted by means of a sodium chloride gradient (0→3M). After regrouping the fractions containing the compound (8), the latter was desalted by passage over the Sephadex G-25 column used above m=3.4 mg. The structure of compound (8) is confirmed by determination of the uronic acid, of the glucosamine and of the sulphates and through its NMR spectrum (see FIG. 3). (The meanings of the symbols used in this Figure are as follows. G denotes the signal of the anomeric carbon at the 1 position of the uronic acid and Aa-1 that of the N-acetyl glucosamine; Aa-6 that of the O-sulphate group at the 6 position of the sulphated glucosamine; A-a2 that of the carbon at the 2 position of the glucosamine unit; OMe, that of the methylglucoside group and MeOH, that of the methanol serving as an internal standard). Its U.V. spectrum has an absorption maximum at 205 nm.

EXAMPLE 5

Preparation of the disaccharides (9) and (10)

To obtain these derivatives, the disaccharide (6) is first subjected to a sulphation reaction to convert the —NH$_2$ group into —NHSO$_3$Na group, then to a saponification reaction of the —COOMe group as indicated above.

The product (6) (14 mg) is dissolved in water (5 ml). The pH is brought to and kept at 9.5 by the addition, controlled automatically, of 0.1N soda. The complex trimethylamine/SO$_3$ (20 mg) is added. After one night, a further addition of complex is made (30 mg). After 24 hours, 1N soda (1 ml) is added and it is left to stand for an hour at room temperature. After passage over a cation exchange resin (Dowex 50 W H$^+$), then neutralization by soda, the compound (10) is purified as described for the compound (8) (desalting, ion exchange, desalting). In this way 2.9 mg of product (10) is obtained. The structure of the product (10) is confirmed by determination of the uronic acid, of the glucosamine and of the sulphates as well as by its NMR spectrum (see FIG. 4). In this Figure, G, OMe, MeOH have the meanings used for FIG. 3, As-1 represents the signal of the anomeric carbon at the 1 position of the N-sulphated glucosamine, As-6 that of the carbon at the 6 position of the sulphated glucosamine and As-2 that of the anomeric carbon of the N-sulphated glucosamine at the 2 position.

We claim:

1. A process for synthesizing a heparinic disaccharide which process comprises the steps of condensing I with II

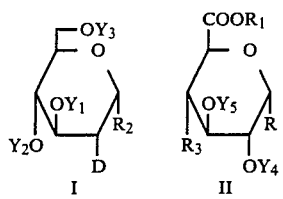

wherein Y groups $Y_1$, $Y_2$, $Y_3$, $Y_4$, and $Y_5$ are selected from the group consisting of a precursor to an $SO_3$ group, and a precursor to an OH group, wherein at least one Y group is a precursor to an $SO_3$ group and at least one Y group is a precursor to an OH group, wherein the precursor to an OH group is stable and does not migrate to other carbon positions during removal of the Y groups which are the precursor to an $SO_3$ group and during the introduction of $SO_3$ groups to replace the Y groups which are the precursor to an $SO_3$ group, further wherein $R_1$ is a protecting group which forms an ester at the carboxyl group, which protecting group is removable following removal of Y groups which are the precusor to an OH group, further wherein R is an inert protecting group, which protecting group is stable during removal of the other protecting groups, further wherein $R_2$ is a reactive group, which reactive group allows the formation of a 1-4 alpha type linkage during the condensation, further wherein $R_3$ is an OH group, further wherein D is a nitrogen containing group, which nitrogen containing group is a precursor to an amine, wherein the process further comprises the steps of removing the Y groups which are the precursor to an $SO_3$ group, substituting $SO_3$ groups at the carbon positions left free thereby, removing the Y groups which are the precursor to an OH group and converting the nitrogen containing group into an amine.

2. The process of claim 1 which further comprises converting the amine group to a group which is selected from the group consisting of $NHCOCH_3$ and $NHSO_3$.

3. The process of claim 1 which further comprises removing the protecting group which forms an ester at the carboxyl and forming a salt with an alkaline metal cation.

4. The process of claim 1 which further comprises forming a salt between an alkaline metal cation and the $SO_3$ groups.

5. The process of claim 1 wherein
the precursor to an $SO_3$ group is acetyl,
the precursor to an OH group is benzyl,
$R_1$ is an alkyl group having from 1 to 4 carbons,
R is selected from the group consisting of an alkyl group having from one to four carbons, and a lower aryl group,
$R_2$ is a halogen,
D is $N_3$.

6. The process of claim 5 wherein $R_2$ is a halogen which is selected from the group consisting of Br and Cl.

7. A process for synthesizing a heparinic disaccharide which process comprises the steps of condensing I with II

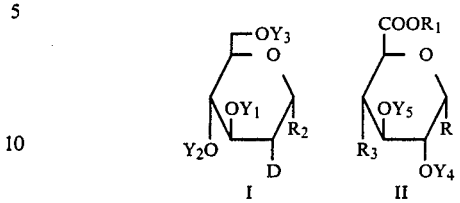

wherein $Y_3$ is a precursor to an $SO_3$ group, and Y groups $Y_1$, $Y_2$, $Y_4$, and $Y_5$ are a precursor to an OH group, wherein the precursor to an OH group is stable and does not migrate to other carbon positions during removal of the precursor to an $SO_3$ group and the introduction of $SO_3$ groups to replace the Y groups which are the precursor to an $SO_3$ group, further wherein $R_1$ is a protecting group which forms an ester at the carboxyl group which protecting group is removable following removal of the Y groups which are the precursor to an OH group, further wherein R is an inert protecting group, which protecting group is stable during removal of the other protecting groups, further wherein $R_2$ is a reactive group, which reactive group allows the formation of a 1-4 alpha type linkage during the condensation, further wherein $R_3$ is an OH group, further wherein D is a nitrogen containing group, which nitrogen containing group is a precursor to an amine, wherein the process further comprises the steps of removing $Y_3$, substituting an $SO_3$ group at the carbon position left free thereby, removing the Y groups which are a precursor to an OH group and converting the nitrogen containing group into an amine.

8. The process of claim 7 which further comprises converting the amine group to a group which is selected from the group consisting of $NHCOCH_3$ and $NHSO_3$.

9. The process of claim 7 which further comprises removing the protecting group which forms an ester at the carboxyl and forming a salt with an alkaline metal cation.

10. The process of claim 7 which further comprises forming a salt between an alkaline metal cation and the $SO_3$ group.

11. The process of claim 7 wherein
the precursor to an $SO_3$ group is acetyl,
the precursor to an OH group is benzyl,
$R_1$ is an alkyl group having from 1 to 4 carbons,
R is selected from the group consisting of an alkyl group having from one to four carbons, and a lower aryl group,
$R_2$ is a halogen,
D is $N_3$.

12. The process of claim 11 wherein $R_2$ is a halogen which is selected from the group consisting of Br and Cl.

13. A process for synthesizing a heparinic disaccharide which process comprises the steps of condensing I with II

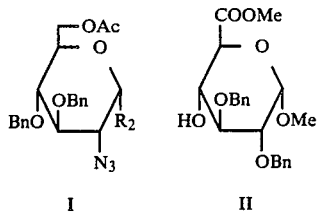

wherein $R_2$ is a halogen, wherein the process further comprises the steps of removing the acetyl group at carbon six of I, substituting an $SO_3$ group at the carbon position left free thereby, removing the benzyl group and converting the $N_3$ group into an amine.

14. The process of claim 13 which further comprises converting the amine group to a group which is selected from the group consisting of $NHCOCH_3$ and $NHSO_3$.

15. The process of claim 14 which further comprises removing the methyl group which forms an ester at the carboxyl and forming a salt with an alkaline metal cation.

16. The process of claim 13 which further comprises forming a salt between an alkaline metal cation and the $SO_3$.

17. The process of claim 13 wherein $R_2$ is a halogen which is selected from the group consisting of Br and Cl.

18. The process of claim 4 wherein the acetylation of the $NH_2$ group is carried out at pH8.

19. The process of claim 14 wherein the sulfatation of the $NH_2$ group is carried out at pH 9-10.

20. The process of claim 13 wherein the condensation reaction is carried out in an organic solvent.

21. The process of claim 20 wherein the organic solvent is dichloromethane.

22. The process of claim 13 wherein the condensation reaction is carried out in the presence of silver triflate.

23. The process of claim 13 wherein the condensation reaction is carried out in the presence of a proton acceptor.

24. The process of claim 23 wherein the proton acceptor is sym-collidine.

25. The process of claim 13 wherein the condensation reaction is carried out in dichloromethane in the presence of silver triflate and sym-collidine.

26. The process of claim 13 further comprising the step, following the substituting of the $SO_3$ group, of passing the compound formed over an $Na^+$ resin.

* * * * *

UNITED STATES PATENT AND TRADEMARK OFFICE
CERTIFICATE OF CORRECTION

PATENT NO. : 4,774,231
DATED : September 27, 1988
INVENTOR(S) : Maurice Petitou, et al It is certified that error appears in the above-identified patent and that said Letters Patent is hereby corrected as shown below:

On the title page the following should be added to the Foreign Application Priority Data:

April 28, 1982 (PCT) PCT.........FR 82 00076

Signed and Sealed this

Seventh Day of November, 1989

Attest:

JEFFREY M. SAMUELS

*Attesting Officer*  *Acting Commissioner of Patents and Trademarks*